US009623348B2

(12) United States Patent
McCarthy et al.

(10) Patent No.: US 9,623,348 B2
(45) Date of Patent: Apr. 18, 2017

(54) REFLECTOR FOR AN ACOUSTOPHORETIC DEVICE

(71) Applicant: FloDesign Sonics, Inc., Wilbraham, MA (US)

(72) Inventors: Brian McCarthy, Ludlow, MA (US); Ben Ross-Johnsrud, Wilbraham, MA (US); Bart Lipkens, Hampden, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 36 days.

(21) Appl. No.: 14/678,841

(22) Filed: Apr. 3, 2015

(65) Prior Publication Data
US 2015/0209695 A1    Jul. 30, 2015

Related U.S. Application Data

(63) Continuation of application No. 14/026,413, filed on Sep. 13, 2013, which is a continuation-in-part of application No. 13/844,754, filed on Mar. 15, 2013.
(Continued)

(51) Int. Cl.
*B01D 29/52* (2006.01)
*B01D 37/00* (2006.01)
(Continued)

(52) U.S. Cl.
CPC ............ *B01D 21/28* (2013.01); *B01D 17/04* (2013.01); *B01D 17/044* (2013.01); *B01J 19/10* (2013.01);
(Continued)

(58) Field of Classification Search
CPC ...... B01D 29/115; B01D 29/52; B01D 37/00; B01D 2201/127
See application file for complete search history.

(56) References Cited

U.S. PATENT DOCUMENTS 2,667,944 A    2/1954 Crites
3,555,311 A *  1/1971 Weber .................. B06B 1/0677
                                                    310/322
(Continued)

FOREIGN PATENT DOCUMENTS

DE    30 27 433 A1    2/1982
EP    0 292 470 B1    11/1988
(Continued)

OTHER PUBLICATIONS

Alvarez et al.; Shock Waves, vol. 17, No. 6, pp. 441-447, 2008.
(Continued)

*Primary Examiner* — Walter D Griffin
*Assistant Examiner* — Cameron J Allen
(74) *Attorney, Agent, or Firm* — Richard M. Klein; Fay Sharpe LLP

(57) ABSTRACT

An apparatus includes a flow chamber having at least one inlet and at least one outlet. At least one ultrasonic transducer is located on a wall of the flow chamber, which operates to create a multi-dimensional acoustic standing wave in the flow chamber. A reflector is located on the wall on the opposite side of the flow chamber from the at least one ultrasonic transducer. The reflector is formed from a thin structure that provides a pressure release boundary, such as a plastic film/air interface.

21 Claims, 9 Drawing Sheets

Related U.S. Application Data

(60) Provisional application No. 61/975,035, filed on Apr. 4, 2014, provisional application No. 61/611,159, filed on Mar. 15, 2012, provisional application No. 61/611,240, filed on Mar. 15, 2012, provisional application No. 61/754,792, filed on Jan. 21, 2013, provisional application No. 61/708,641, filed on Oct. 2, 2012.

(51) Int. Cl.
| | | |
|---|---|---|
| *B01D 21/28* | (2006.01) | |
| *B01D 17/04* | (2006.01) | |
| *B01J 19/10* | (2006.01) | |
| *B06B 1/06* | (2006.01) | |
| *C12M 1/42* | (2006.01) | |
| *C12M 1/00* | (2006.01) | |

(52) U.S. Cl.
CPC .......... *B06B 1/0644* (2013.01); *C12M 35/04* (2013.01); *B01J 2219/0869* (2013.01); *C12M 47/02* (2013.01)

(56) References Cited

U.S. PATENT DOCUMENTS

| | | |
|---|---|---|
| 4,055,491 A | 10/1977 | Porath-Furedi |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,398,325 A | 8/1983 | Piaget et al. |
| 4,666,595 A | 5/1987 | Graham |
| 4,699,588 A | 10/1987 | Zinn et al. |
| 4,743,361 A | 5/1988 | Schram |
| 4,759,775 A | 7/1988 | Peterson et al. |
| 4,983,189 A | 1/1991 | Peterson et al. |
| 5,225,089 A | 7/1993 | Benes et al. |
| 5,371,429 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A * | 9/1995 | Spevak ............... G10K 13/00 310/328 |
| 5,484,537 A | 1/1996 | Whitworth |
| 5,527,460 A | 6/1996 | Trampler et al. |
| 5,560,362 A | 10/1996 | Sliwa, Jr. et al. |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A * | 1/1998 | Trampler ............. B01D 21/283 210/748.05 |
| 5,831,166 A | 11/1998 | Kozuka et al. |
| 5,902,489 A | 5/1999 | Yasuda et al. |
| 5,912,182 A | 6/1999 | Coakley et al. |
| 5,951,456 A | 9/1999 | Scott |
| 6,090,295 A | 7/2000 | Raghavarao et al. |
| 6,166,231 A | 12/2000 | Hoeksema |
| 6,205,848 B1 | 3/2001 | Faber et al. |
| 6,216,538 B1 | 4/2001 | Yasuda et al. |
| 6,332,541 B1 | 12/2001 | Coakley et al. |
| 6,391,653 B1 | 5/2002 | Letcher et al. |
| 6,487,095 B1 | 11/2002 | Malik et al. |
| 6,592,821 B1 | 7/2003 | Wada et al. |
| 6,649,069 B2 | 11/2003 | DeAngelis |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,837,040 B2 | 11/2010 | Ward et al. |
| 7,846,382 B2 | 12/2010 | Strand et al. |
| 7,968,049 B2 | 6/2011 | Takahashi et al. |
| 8,080,202 B2 | 12/2011 | Takahashi et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,679,338 B2 | 3/2014 | Rietman et al. |
| 2002/0134734 A1 | 9/2002 | Campbell et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1* | 2/2004 | Diaz .................... G01N 29/024 73/597 |
| 2005/0196725 A1 | 9/2005 | Fu |
| 2006/0037915 A1 | 2/2006 | Strand et al. |
| 2007/0272618 A1 | 11/2007 | Gou et al. |
| 2007/0284299 A1 | 12/2007 | Xu et al. |
| 2008/0217259 A1 | 9/2008 | Siversson |
| 2009/0029870 A1 | 1/2009 | Ward et al. |
| 2009/0045107 A1 | 2/2009 | Ward et al. |
| 2009/0053686 A1 | 2/2009 | Ward et al. |
| 2009/0098027 A1 | 4/2009 | Tabata et al. |
| 2009/0178716 A1 | 7/2009 | Kaduchak et al. |
| 2009/0194420 A1 | 8/2009 | Mariella, Jr. et al. |
| 2009/0295505 A1 | 12/2009 | Mohammadi et al. |
| 2010/0000945 A1 | 1/2010 | Gavalas |
| 2010/0078384 A1 | 4/2010 | Yang |
| 2010/0124142 A1 | 5/2010 | Laugharn et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0317088 A1 | 12/2010 | Radaelli et al. |
| 2010/0323342 A1 | 12/2010 | Gonz lez Gomez et al. |
| 2010/0330633 A1 | 12/2010 | Walther et al. |
| 2011/0024335 A1 | 2/2011 | Ward et al. |
| 2011/0092726 A1 | 4/2011 | Clarke |
| 2011/0123392 A1 | 5/2011 | Dionne et al. |
| 2011/0154890 A1 | 6/2011 | Holm et al. |
| 2011/0166551 A1 | 7/2011 | Schafer |
| 2011/0262990 A1 | 10/2011 | Wang et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0328477 A1* | 12/2012 | Dionne ................ B06B 1/0625 422/128 |
| 2012/0329122 A1 | 12/2012 | Lipkens et al. |
| 2013/0277316 A1 | 10/2013 | Dutra et al. |
| 2013/0284271 A1 | 10/2013 | Lipkens et al. |
| 2014/0011240 A1 | 1/2014 | Lipkens et al. |

FOREIGN PATENT DOCUMENTS

| | | |
|---|---|---|
| EP | 1 254 669 B1 | 11/2002 |
| GB | 2 420 510 A | 5/2006 |
| WO | WO 1987/07178 A1 | 12/1987 |
| WO | WO 02/072234 A1 | 9/2002 |
| WO | WO 2009/111276 A1 | 9/2009 |
| WO | WO 2009/144709 A1 | 12/2009 |

(56) References Cited

FOREIGN PATENT DOCUMENTS

| WO | WO 2010/024753 A1 | 4/2010 |
|----|-------------------|--------|
| WO | WO 2011/023949 A2 | 3/2011 |
| WO | WO 2011/027146 A2 | 3/2011 |
| WO | WO 2011/161463 A2 | 12/2011 |

OTHER PUBLICATIONS

Benes et al.; Ultrasonic Separation of Suspended Particles, 2001 IEEE Ultrasonics Symposium; Oct. 7-10, 2001; pp. 649-659; Atlanta, Georgia.

Castro; Tunable gap and quantum quench dynamics in bilayer graphene; Jul. 13, 2010; Mathematica Summer School.

Cravotto et al.; Ultrasonics Sonochemistry, vol. 15, No. 5, pp. 898-902, 2008.

Garcia-Lopez, et al; Enhanced Acoustic Separation of Oil-Water Emulsion in Resonant Cavities. The Open Acoustics Journal. 2008, vol. 1, pp. 66-71.

Gor'Kov; On the forces acting on a small particle in an acoustical field in an ideal fluid; Soy. Phys. Dokl.; vol. 6, pp. 773-775; 1962.

Hill et al.; Ultrasonic Particle Manipulation; Microfluidic Technologies for Miniaturized Analysis Systems, Jan. 2007, pp. 359-378.

Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.

Latt et al.; Ultrasound-membrane hybrid processes for enhancement of filtration properties; Ultrasonics sonochemistry 13.4 (2006): 321-328.

Lipkens et al.; Frequency sweeping and fluid flow effects on particle trajectories in ultrasonic standing waves; Acoustics 08, Paris, Jun. 29-Jul. 4, 2008.

Lipkens et al.; Prediction and measurement of particle velocities in ultrasonic standing waves; J. Acoust. Soc. Am., 124 No. 4, pp. 2492 (A) 2008.

Lipkens et al.; Separation of micron-sized particles in macro-scale cavities by ultrasonic standing waves; Presented at the International Congress on Ultrasonics, Santiago; Jan. 11-17, 2009.

Lipkens et al.; The effect of frequency sweeping and fluid flow on particle trajectories in ultrasonic standing waves; IEEE Sensors Journal, vol. 8, No. 6, pp. 667-677, 2008.

Lipkens et al., Macro-scale acoustophoretic separation of lipid particles from red blood cells, the Journal of the Acoustical Society of America, vol. 133, Jun. 2, 2013, p. 045017, XP055162509, New York, NY.

Meribout et a.; An Industrial-Prototype Acoustic Array for Real-Time Emulsion Layer Detection in Oil Storage Tanks; IEEE Sensors Journal, vol. 9, No. 12, Dec. 2009.

Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.

Pangu et al.; Droplet transport and coalescence kinetics in emulsions subjected to acoustic fields; Ultrasonics 46, pp. 289-302 (2007).

Ponomarenko et al.; Density of states and zero Landau level probed through capacitance of graphene; Nature Nanotechnology Letters, Jul. 5, 2009; DOI: 10.1038/NNAN0.2009.177.

Seymour et al, J. Chem. Edu., 1990, 67(9), p. 763, published Sep. 1990.

Annex to Form PCT/ISA/206—Communication Relating to the Results of the Partial International Search Report, dated Jul. 18, 2013.

European Search Report of European Application No. 11769474.5 Dated Oct. 10, 2012.

International Search Report and Written Opinion dated Dec. 20, 2011, for corresponding PCT application No. PCT/US2011/032181.

International Search Report and Written Opinion dated Feb. 27, 2012, for PCT application No. PCT/US2011/040787.

International Search Report and Written Opinion of International Application No. PCT/US2013/037404 Dated Jun. 21, 2013.

International Search Report and Written Opinion of International Application No. PCT/US2013/050729 Dated Sep. 25, 2013.

International Search Report for corresponding PCT Application Serial No. PCT/US2014/015382 dated May 6, 2014.

Phys. Org. "Engineers develop revolutionary nanotech water desalination membrane." Nov. 6, 2006. http://phys.org/news82047372.html.

"Proceedings of the Acoustics 2012 Nantes Conference," Apr. 23-27, 2012, Nantes, France, pp. 278-282.

Sony New Release: <http://www.sony.net/SonyInfo/News/Press/201010/10-137E/index.html>.

\* cited by examiner

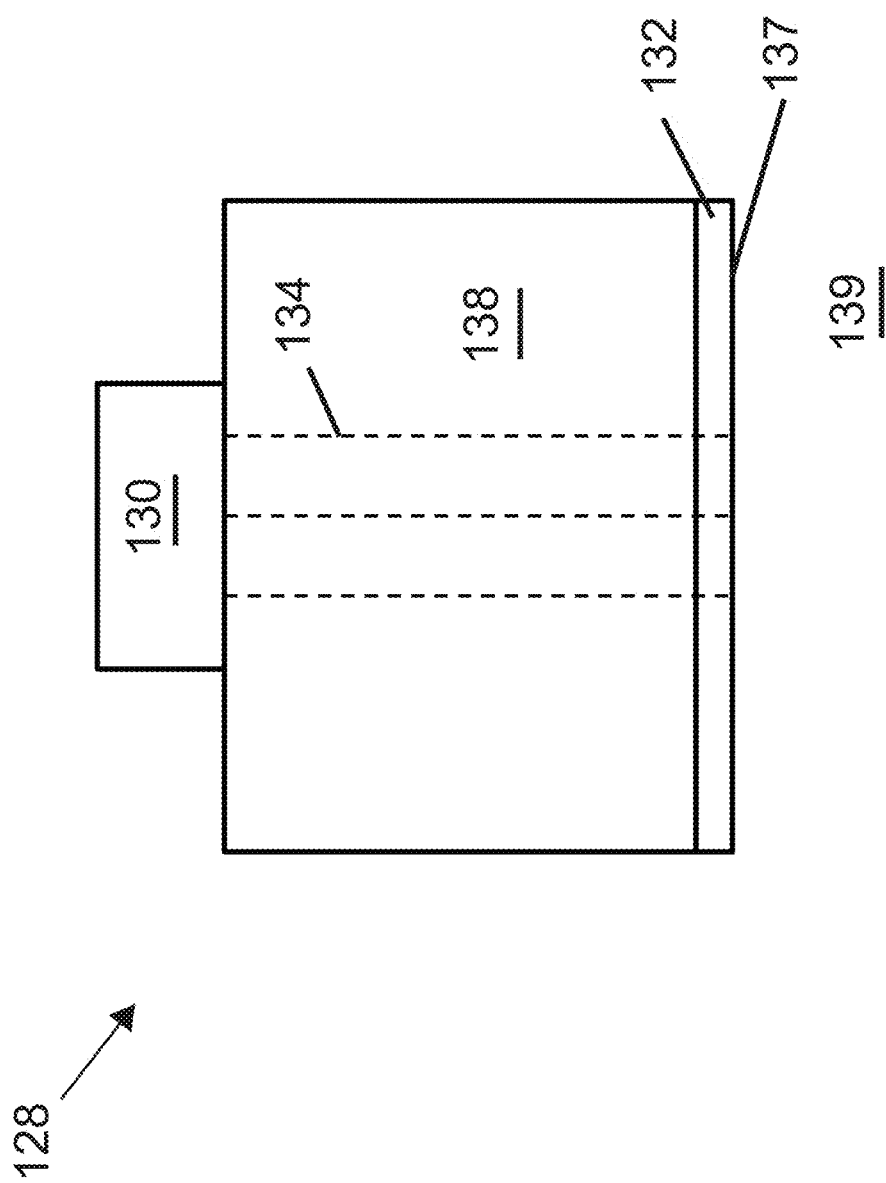

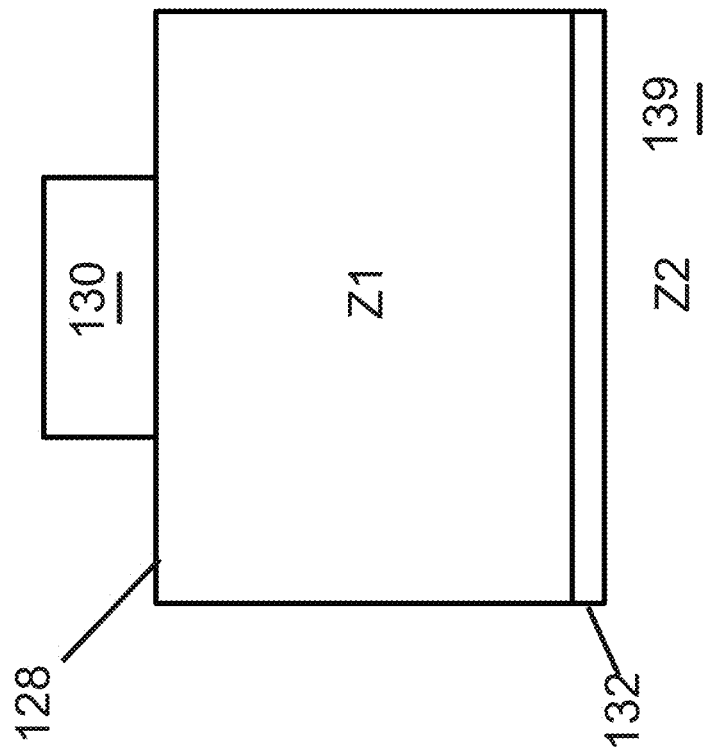

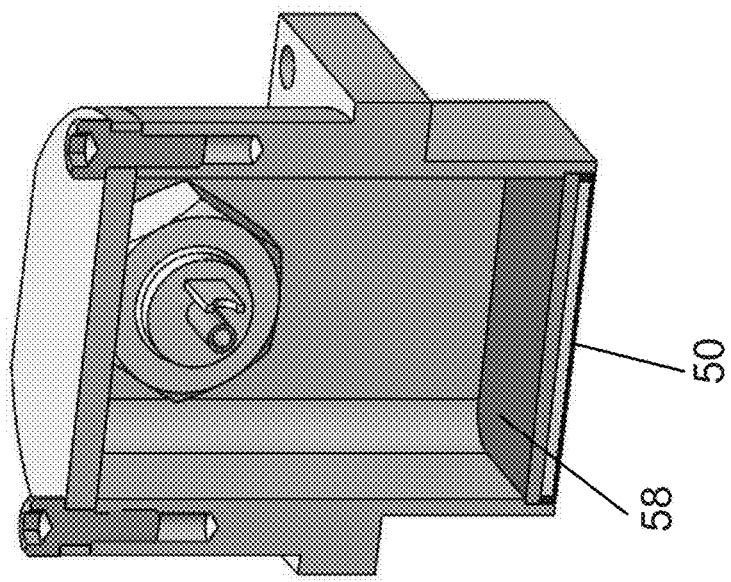
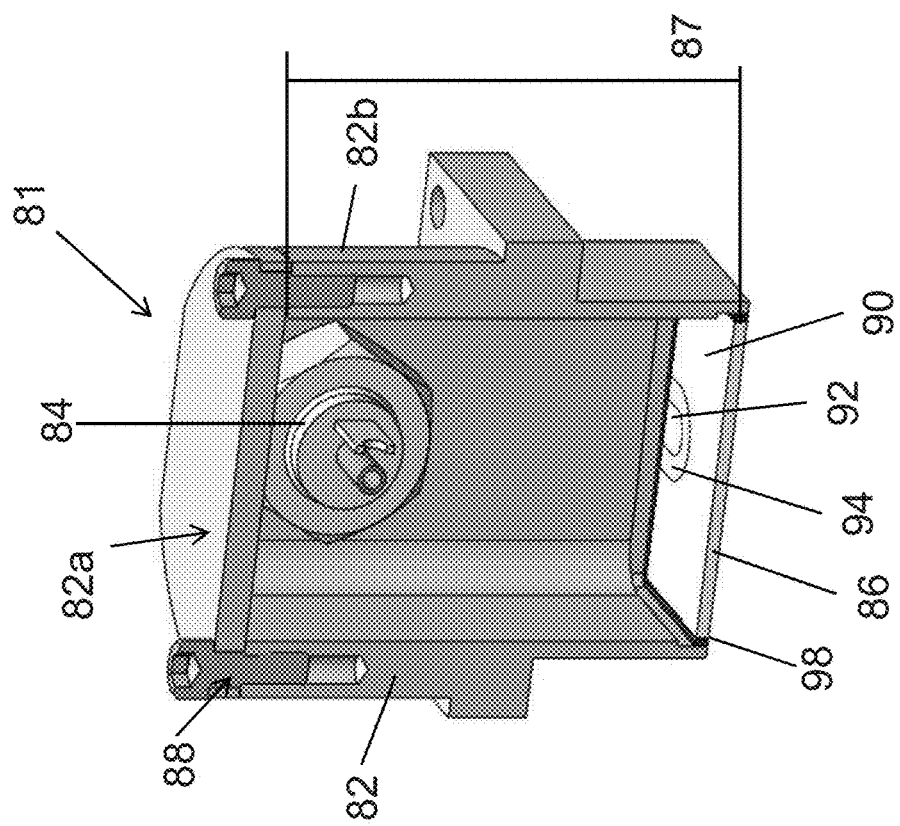

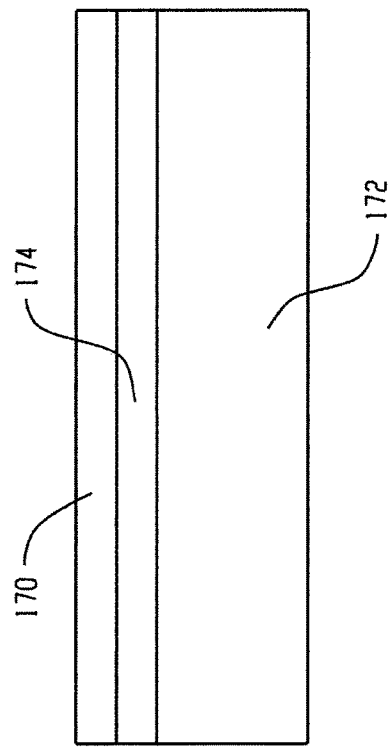
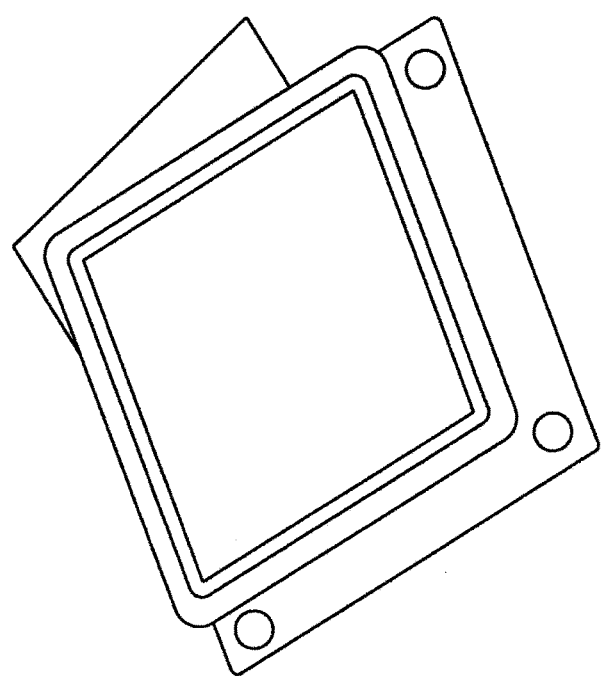
Fig. 11

REFLECTOR FOR AN ACOUSTOPHORETIC DEVICE

CROSS-REFERENCE TO RELATED APPLICATIONS

The present application claims the benefit of U.S. Provisional Patent Application Ser. No. 61/975,035, filed Apr. 4, 2014, which is incorporated herein by reference in its entirety. This application is also a continuation-in-part of U.S. patent application Ser. No. 14/026,413, filed on Sep. 13, 2013 U.S. patent application Ser. No. 14/026,413 is a continuation-in-part of U.S. Ser. No. 13/844,754, filed Mar. 15, 2013, which claimed the benefit of U.S. Provisional Patent Application Ser. No. 61/611,159, filed Mar. 15, 2012, and of U.S. Provisional Patent Application Ser. No. 61/611,240, also filed Mar. 15, 2012, and of U.S. Provisional Patent Application Ser. No. 61/708,641, filed on Oct. 2, 2012, and of U.S. Provisional Patent Application Ser. No. 61/754,792, filed Jan. 21, 2013. These applications are incorporated herein by reference in their entireties.

BACKGROUND

The ability to separate a particle/fluid mixture into its separate components is desirable in many applications. Acoustophoresis is the separation of particles using high intensity sound waves, and without the use of membranes or physical size exclusion filters. It has been known that high intensity standing waves of sound can exert forces on particles in a fluid when there is a differential in both density and/or compressibility, otherwise known as the acoustic contrast factor. The pressure profile in a standing wave contains areas of local minimum pressure amplitudes at its nodes and local maxima at its anti-nodes. Depending on the density and compressibility of the particles, they will be trapped at the nodes or anti-nodes of the standing wave. The higher the frequency of the standing wave, the smaller the particles that can be trapped due the pressure of the standing wave.

Growth in the field of biotechnology has been due to many factors, some of which include the improvements in the equipment available for bioreactors. Improvements in equipment have allowed for larger volumes and lower cost for the production of biologically derived materials such as monoclonal antibodies and recombinant proteins. One of the key components used in the manufacturing processes of new biologically based pharmaceuticals is the bioreactor and the ancillary processes associated therewith.

A modern bioreactor is a very complicated piece of equipment. It provides for, among other parameters, the regulation of fluid flow rates, gas content, temperature, pH and oxygen content. All of these parameters can be tuned to allow the cell culture to be as efficient as possible of producing the desired biomolecules from the bioreactor process. One process for using a bioreactor is the perfusion process. The perfusion process is distinguished from the batch and fed-batch processes by its lower capital cost and higher throughput.

In the fed-batch process, a culture is seeded in a bioreactor. The gradual addition of a fresh volume of selected nutrients during the growth cycle is used to improve productivity and growth. The product, typically a monoclonal antibody or a recombinant protein, is recovered after the culture is harvested. Separating the cells, cell debris and other waste products from the desired product is currently performed using various types of filters for separation. Such filters are expensive and become clogged and non-functional as the bioreactor material is processed. A fed-batch bioreactor also has high start-up costs, and generally requires a large volume to obtain a cost-effective amount of product at the end of the growth cycle, and such processes include large amounts of non-productive downtime.

A perfusion bioreactor processes a continuous supply of fresh media that is fed into the bioreactor while growth-inhibiting byproducts are constantly removed. The nonproductive downtime can be reduced or eliminated with a perfusion bioreactor process. The cell densities achieved in perfusion culture (30-100 million cells/mL) are typically higher than for fed-batch modes (5-25 million cells/mL). However, a perfusion bioreactor requires a cell retention device to prevent escape of the culture when byproducts are being removed. These cell retention systems add a level of complexity to the perfusion process, requiring management, control, and maintenance for successful operation. Operational issues such as malfunction or failure of the cell retention equipment has previously been a problem with perfusion bioreactors. This has limited their attractiveness in the past.

It would be desirable to provide means that can reduce the cost and effort of using bioreactors and separating the desired products from the cells that make them.

BRIEF DESCRIPTION

The present disclosure relates, in various embodiments, to systems for producing biomolecules such as recombinant proteins or monoclonal antibodies, and to processes for separating these desirable products from a cell culture in a disposable or non-disposable bioreactor system. Generally, the bioreactor includes an acoustophoretic device for producing multi-dimensional acoustic standing waves, which is located near an outlet port for the bioreactor. Such standing waves are produced by an ultrasonic transducer and a reflector. In the present disclosure, the reflector is formed from a thin material that is essentially acoustically transparent, such as certain plastic films, rather than a solid metal. The thin material provides a constant pressure boundary, also known as a free surface. In essence, these embodiments are examples of providing a pressure release surface, such as from a transparent layer of a plastic film.

Disclosed in various embodiments are apparatuses that include a flow chamber having at least one inlet and at least one outlet. At least one ultrasonic transducer is located on a wall of the flow chamber. The transducer includes a piezoelectric material driven by a voltage signal to create a multi-dimensional acoustic standing wave in the flow chamber. A thin structure is located on the wall on the opposite side of the flow chamber from the at least one ultrasonic transducer. The thin structure provides a pressure release boundary that acts as a reflector.

In particular embodiments, the thin structure is a plastic film. The plastic film can be made from a material selected from the group consisting of olefins, polyurethanes, polyureas, polyesters, polystyrenes, polyamides, cellulosics, ionomers, polyvinyl chloride, polyvinyl butyral, polyvinylidene fluoride, polyvinylidene chloride, ethylene vinyl acetate, ethylene tetrafluoroethylene, polytetrafluoroethylene, and combinations thereof. More specifically, the plastic film can be a polypropylene.

The thin structure can be optically transparent. The thin structure may be substantially flat. The thin structure may have a thickness that is ½ or less of the wavelength relative to the frequency emitted by the at least one ultrasonic transducer. Generally, this thickness is in the range of 10 microns to 1 millimeter (mm).

The transducer may have a housing containing the piezoelectric material. The piezoelectric material may be air backed, i.e. does not have a backing layer. The piezoelectric material may be a ceramic crystal.

In other embodiments, the piezoelectric material is backed by a substantially acoustically transparent material. The substantially acoustically transparent material may be balsa wood, cork, or a foam. The substantially acoustically transparent material can have a thickness of up to one inch. The substantially acoustically transparent material may be in the form of a lattice.

In some embodiments, the ultrasonic transducer may have a face that contacts fluid within the flow chamber, the face being coated with a wear layer comprising chrome, electrolytic nickel, electroless nickel, p-xylylene, glassy carbon, or urethane.

The apparatus may further include an apparatus inlet that leads to an annular plenum, a contoured nozzle wall downstream of the apparatus inlet, a collection duct surrounded by the annular plenum, and a connecting duct joining the contoured nozzle wall to the flow chamber inlet.

The device can comprise a plurality of transducers that span the width of the flow chamber.

Also disclosed in various embodiments are methods of separating a second fluid or a particulate from a host fluid, comprising: flowing a mixture of the host fluid and the second fluid or particulate through an apparatus, the apparatus comprising: a flow chamber having at least one inlet and at least one outlet; at least one ultrasonic transducer located on a wall of the flow chamber, the transducer including a piezoelectric material driven by a voltage signal to create a multi-dimensional acoustic standing wave in the flow chamber; and a thin structure located on the wall on the opposite side of the flow chamber from the at least one ultrasonic transducer, the thin structure providing a pressure release boundary that acts as a reflector; and capturing smaller particles of the second fluid or particulate in the multi-dimensional acoustic standing wave to separate the second fluid or particulate from the host fluid. The secondary fluid or particles cluster or coalesce at specific points such that gravity separation eventually and continuously occurs. In other words, once the clustering, coalescing or clumping occurs, continuous gravity separation happens. A pulsed voltage signal drives the at least one ultrasonic transducer.

The particulate may be Chinese hamster ovary (CHO) cells, NS0 hybridoma cells, baby hamster kidney (BHK) cells, insect cells or human cells such as stem cells and T-cells. The mixture may be continuously flowed through the flow chamber. The standing wave may have an axial force and a lateral force, the lateral force being at least the same order of magnitude as the axial force.

Also disclosed in various embodiments are apparatuses that include a flow chamber having at least one inlet and at least one outlet. At least one ultrasonic transducer is located on a wall of the flow chamber. The transducer includes a piezoelectric material driven by a voltage signal to create a multi-dimensional acoustic standing wave in the flow chamber. A thin structure is located on the wall on the opposite side of the flow chamber from the at least one ultrasonic transducer. The thin structure provides a pressure release boundary that acts as a reflector. The apparatus has an acoustic reflection coefficient of −0.1 to −1.0.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 1 is a schematic plan view of a flow chamber, illustrating the thin structure/reflector of the present disclosure.

FIG. 2 is a schematic showing how the acoustic reflection coefficient is calculated for the device of FIG. 1.

FIG. 6 is a cross-sectional diagram of an ultrasonic transducer of the present disclosure. An air gap is present within the transducer, and no backing layer or wear plate is present.

FIG. 7 is a cross-sectional diagram of an ultrasonic transducer of the present disclosure. An air gap is present within the transducer, and a backing layer and wear plate are present.

FIG. 11 is a picture of a test ultrasonic transducer having an acoustically transparent film cover.

DETAILED DESCRIPTION

Figure 3A:
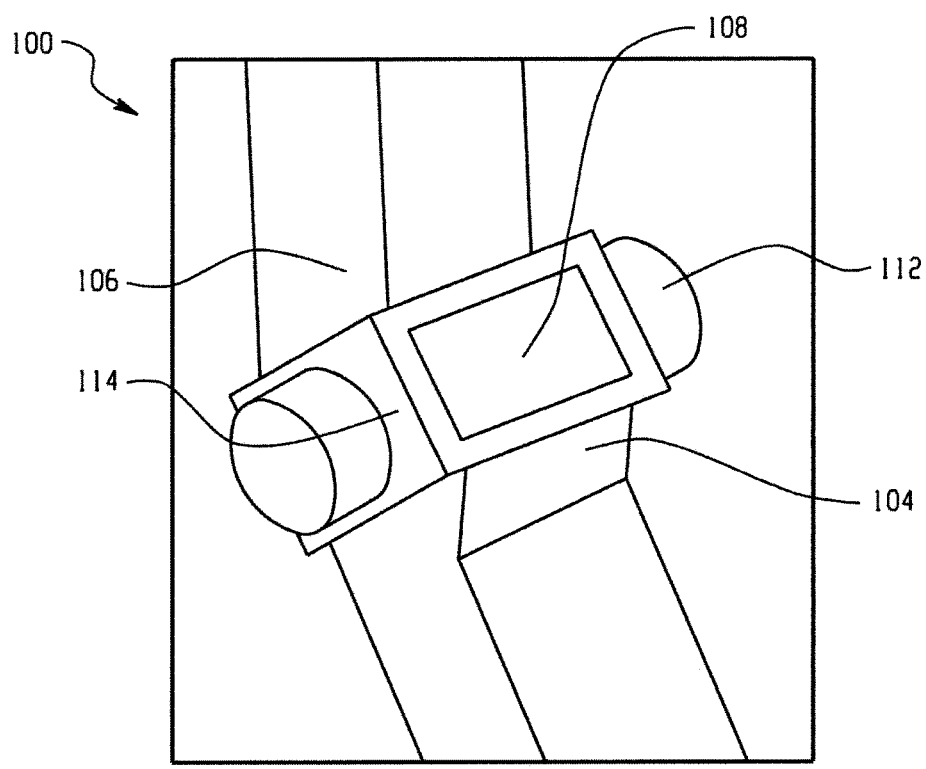
FIG. 3A is a picture of an acoustophoretic separator having one ultrasonic transducer and a transparent thin plastic film acting as the reflector.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named components/steps and allowing the presence of other components/steps. The term "comprising" should be construed to include the term "consisting of", which allows the presence of only the named components/ steps, along with any impurities that might result from the manufacture of the named components/steps.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The terms "substantially" and "about" can be used to include any numerical value that can vary without changing the basic function of that value. When used with a range, "substantially" and "about" also disclose the range defined by the absolute values of the two endpoints, e.g. "about 2 to about 4" also discloses the range "from 2 to 4." The terms "substantially" and "about" may refer to plus or minus 10% of the indicated number.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "upwards" and "downwards" are also relative to an absolute reference; an upwards flow is always against the gravity of the earth.

The present application refers to "the same order of magnitude." Two numbers are of the same order of magnitude if the quotient of the larger number divided by the smaller number is a value less than 10.

The acoustophoretic separation technology of the present disclosure employs ultrasonic acoustic standing waves to trap, i.e., hold stationary, particles or a secondary fluid in a host fluid stream. The particles or secondary fluid collect at the nodes or anti-nodes of the multi-dimensional acoustic standing wave, depending on the particles' or secondary fluid's acoustic contrast factor relative to the host fluid, forming clusters that eventually fall out of the multi-dimensional acoustic standing wave when the clusters have grown to a size large enough to overcome the holding force of the multi-dimensional acoustic standing wave (e.g. by coalescence or agglomeration). This is an important distinction from previous approaches where particle trajectories were merely altered by the effect of the acoustic radiation force. The scattering of the acoustic field off the particles results in a three dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable axial positions within the standing waves. When the acoustic radiation force exerted on the particles is stronger than the combined effect of fluid drag force and buoyancy and gravitational force, the particle is trapped within the acoustic standing wave field. This results in concentration, agglomeration and/or coalescence of the trapped particles. The strong lateral forces create rapid clustering of particles. Relatively large solids of one material can thus be separated from smaller particles of a different material, the same material, and/or the host fluid through enhanced gravitational separation.

One specific application for the acoustophoresis device is in the processing of bioreactor materials. It is important to be able to filter all of the cells and cell debris from the expressed materials that are in the fluid stream. The expressed materials are composed of biomolecules such as recombinant proteins or monoclonal antibodies, and are the desired product to be recovered. Through the use of acoustophoresis, the separation of the cells and cell debris is very efficient and leads to very little loss of the expressed materials. This is an improvement over current filtration processes (depth filtration, tangential flow filtration, and the like), which show limited efficiencies at high cell densities, so that the loss of the expressed materials in the filter beds themselves can be up to 5% of the materials produced by the bioreactor. The use of mammalian cell cultures including Chinese hamster ovary (CHO), NS0 hybridoma cells, baby hamster kidney (BHK) cells, and human cells has proven to be a very efficacious way of producing/expressing the recombinant proteins and monoclonal antibodies required of today's pharmaceuticals. The filtration of the mammalian cells and the mammalian cell debris through acoustophoresis aids in greatly increasing the yield of the bioreactor. The acoustophoresis process, through the use of multidimensional acoustic waves, may also be coupled with a standard filtration process upstream or downstream, such as depth filtration using diatomaceous earth, tangential flow filtration (TFF), or other physical filtration processes.

In this regard, the contrast factor is the difference between the compressibility and density of the particles and the fluid itself. These properties are characteristic of the particles and the fluid themselves. Most cell types present a higher density and lower compressibility than the medium in which they are suspended, so that the acoustic contrast factor between the cells and the medium has a positive value. As a result, the axial acoustic radiation force (ARF) drives the cells, with a positive contrast factor, to the pressure nodal planes, whereas cells or other particles with a negative contrast factor are driven to the pressure anti-nodal planes. The radial or lateral component of the acoustic radiation force trap the cells. The radial or lateral component of the ARF is larger than the combined effect of fluid drag force and gravitational force. The radial or lateral component drives the cells/particles to planes where they can cluster into larger groups, which will then gravity separate from the fluid.

As the cells agglomerate at the nodes of the standing wave, there is also a physical scrubbing of the cell culture media that occurs whereby more cells are trapped as they come in contact with the cells that are already held within the standing wave. This generally separates the cells from the cell culture media. The expressed biomolecules remain in the nutrient fluid stream (i.e. cell culture medium).

Desirably, the ultrasonic transducer(s) generate a three-dimensional or multi-dimensional acoustic standing wave in the fluid that exerts a lateral force on the suspended particles to accompany the axial force so as to increase the particle trapping and clumping capabilities of the standing wave. Typical results published in literature state that the lateral force is two orders of magnitude smaller than the axial force. In contrast, the technology disclosed in this application provides for a lateral force to be higher, up to the same order of magnitude as the axial force.

For three-dimensional acoustic fields, Gor'kov's formulation can be used to calculate the acoustic radiation force $F_{ac}$ applicable to any sound field. The primary acoustic radiation force $F_{ac}$ is defined as a function of a field potential U, $$F_A = -\nabla(U),$$

where the field potential U is defined as $$U = V_0 \left[ \frac{\langle p^2 \rangle}{2\rho_f c_f^2} f_1 - \frac{3\rho_f \langle u^2 \rangle}{4} f_2 \right],$$

and $f_1$ and $f_2$ are the monopole and dipole contributions defined by $$f_1 = 1 - \frac{1}{\Lambda \sigma^2},$$

$$f_2 = \frac{2(\Lambda - 1)}{2\Lambda + 1},$$

where p is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o$ is the volume of the cell, and < > indicates time averaging over the period of the wave. Gor'kov's formulation applies to particles smaller than the wavelength. For larger particle sizes, Ilinskii provides equations for calculating the 3D acoustic radiation forces for any particle size. See Ilinskii, *Acoustic Radiation Force on a Sphere in Tissue*, The Journal of the Acoustical Society of America, 132, 3, 1954 (2012), which is incorporated herein by reference.

Perturbation of the piezoelectric crystal in an ultrasonic transducer in a multimode fashion allows for generation of a multidimensional acoustic standing wave. A piezoelectric crystal can be specifically designed to deform in a multi-mode fashion at designed frequencies, allowing for generation of a multi-dimensional acoustic standing wave. The multi-dimensional acoustic standing wave may be generated by distinct modes of the piezoelectric crystal such as the 3×3 mode that would generate multidimensional acoustic standing waves. A multitude of multidimensional acoustic standing waves may also be generated by allowing the piezoelectric crystal to vibrate through many different mode shapes. Thus, the crystal would excite multiple modes such as a 0×0 mode (i.e. a piston mode) to a 1×1, 2×2, 1×3, 3×1, 3×3, and other higher order modes and then cycle back through the lower modes of the crystal (not necessarily in straight order). This switching or dithering of the crystal between modes allows for various multidimensional wave shapes, along with a single piston mode shape to be generated over a designated time.

It is also possible to drive multiple ultrasonic transducers with arbitrary phasing. In other words, the multiple transducers may work to separate materials in a fluid stream while being out of phase with each other. Alternatively, a single ultrasonic transducer that has been divided into an ordered array may also be operated such that some components of the array will be out of phase with other components of the array.

It may be necessary, at times, due to acoustic streaming, to modulate the frequency or voltage amplitude of the standing wave. This may be done by amplitude modulation and/or by frequency modulation. The duty cycle of the propagation of the standing wave may also be utilized to achieve certain results for trapping of materials. In other words, the acoustic beam may be turned on and shut off at different frequencies to achieve desired results.

The lateral force of the total acoustic radiation force (ARF) generated by the ultrasonic transducers of the present disclosure is significant and is sufficient to overcome the fluid drag force at high linear velocities up to 1 cm/s and beyond. For example, linear velocities through the devices of the present disclosure can be a minimum of 4 cm/min for separation of cells/particles, and can be as high as 1 cm/sec for separation of oil/water phases. Flow rates can be a minimum of 25 mL/min, and can range as high as 40 mL/min to 1000 mL/min, or even higher. This is true for batch reactors, fed-batch bioreactors and perfusion bioreactors.

The present disclosure relates to acoustophoretic devices and structures which can make such devices more economical and also provide the opportunity to enhance the range of applications in which they can be used. In this regard, FIG. 1 is a plan (top) view of a flow chamber 128. An ultrasonic transducer 130 is present on one wall of the flow chamber, and a reflector 132 is present on the wall opposite the transducer. Fluid flow is in/out of the plane of the figure.

Reflectors are typically made from a solid material, such as a steel or aluminum plate. While a metal plate provides good reflection, it also adds weight to the flow chamber 128. In the present disclosure, the reflector 132 is a thin structure that can provide a pressure release boundary. A pressure release boundary occurs when the acoustic pressure is zero at the interface.

As illustrated here in FIG. 1, the thin structure 132 has a substantially flat profile relative to the chamber 128. The thin structure separates the fluid 138 inside the flow chamber 128 from the medium (typically air) 139 on the exterior of the flow chamber 128. In operation, the ultrasonic propagating wave 134 (illustrated as dotted lines) is generated by the ultrasonic transducer 130 will reflect off the boundary 137 created at the reflector/air interface. In other words, the wavelength of the standing wave will pass through the material of the reflector, and then reflect off the boundary 137. Thus, the thin structure 132 should be made from an acoustically transparent material, i.e. will not impede the ultrasonic wave or have very low impedance. It is noted that the acoustic wave actually reflects off the air, i.e. at the interface of the thin structure and the air. For purposes of this disclosure, the term "reflector" can be used to refer to the structural component that separates the interior of the flow chamber from the exterior of the flow chamber and provides the interface with the air. However, for example, in particular embodiments, the transducer may be vertically oriented with the multi-dimensional acoustic standing wave propagating upwards into the fluid from the transducer. In this case, the fluid-air boundary will be the free surface providing a pressure release boundary, with no other physical structure necessary.

In specific embodiments, the thin structure has a thickness that is ½ or less of the wavelength of the ultrasonic transducer that it is being used with, and in more particular embodiments is at most 1/20 or at most 1/50 of the wavelength. Generally, this means the thin structure has a thickness of 10 microns to 1 millimeter.

In specific embodiments, the thin structure that provides the pressure release boundary is an acoustically transparent film, such as a plastic film. The plastic film is typically stretched within a frame. The plastic film can be transparent, thereby allowing visualization of the interior of the flow chamber 128. The plastic film can be made of a material selected from the group consisting of olefins, polyurethanes, polyureas, polyesters, polystyrenes, polyamides, cellulosics, ionomers, polyvinyl chloride, polyvinyl butyral, polyvinylidene fluoride, polyvinylidene chloride, ethylene vinyl acetate, ethylene tetrafluoroethylene, polytetrafluoroethylene, and combinations thereof.

FIG. 2 is a schematic explaining the operation of the thin structure that provides the pressure release boundary. The flow chamber 128 is depicted, as is the transducer 130 and the thin structure 132. During operation, the flow chamber is filled with a fluid, typically water, that has an acoustic impedance Z1, which is the product of the density of the fluid and the speed of sound in the fluid. When the thin structure is very thin, its acoustic impedance can be ignored. The medium 139 outside of the flow chamber (typically air) also has an acoustic impedance Z2. As illustrated on the right-hand side, the fluid inside the chamber and the medium outside the chamber result in a system having an acoustic reflection coefficient R that is determined according to the formula:

$$R = \frac{Z2 - Z1}{Z2 + Z1}$$

The acoustic impedance is measured in Rayls (1 Rayl=1 kg/m²/sec). As an example of the efficacy of the thin structure, the acoustic impedance of air at 0° C. is 428 Rayls, and the acoustic impedance of fresh water is 1.48 million Rayls. Thus, the system would have an acoustic reflection coefficient of −0.999. This indicates that most of the acoustic energy will be reflected with a 180 degree phase change.

Figure 3B:
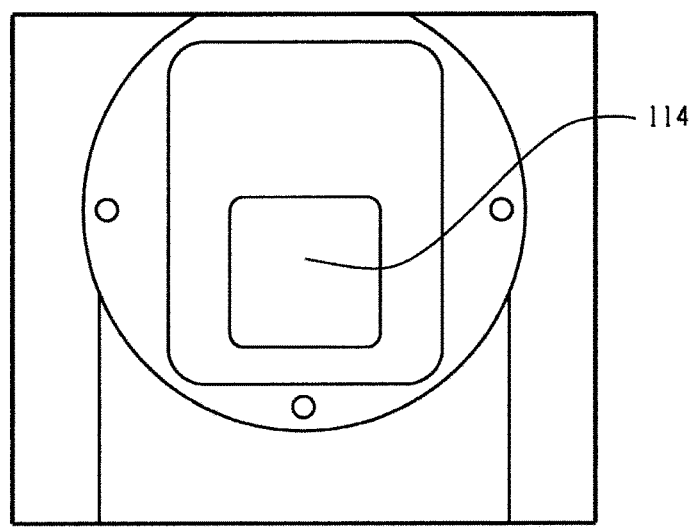
FIG. 3B is a picture showing the thin plastic film reflector.

Pictures showing an acoustophoretic particle separator 100 using an acoustically transparent film as a reflector are shown in FIG. 3A and FIG. 3B. Referring first to FIG. 3A, a multi-component liquid stream (e.g. water or other fluid) enters the inlet 104 and separated fluid exits at the opposite end via outlet 106. It should be noted that this liquid stream is usually under pressure when flowing through the separator. The particle separator 100 has a longitudinal flow channel 108 that carries the multi-component liquid stream past an ultrasonic transducer 112 and the acoustically transparent film 114, which is located on the wall opposite the transducer. As seen here, a thin plastic film was used as the interface between the air and the fluid within the flow chamber. FIG. 3B is a picture of the plastic film during operation of the device.

Figure 4:
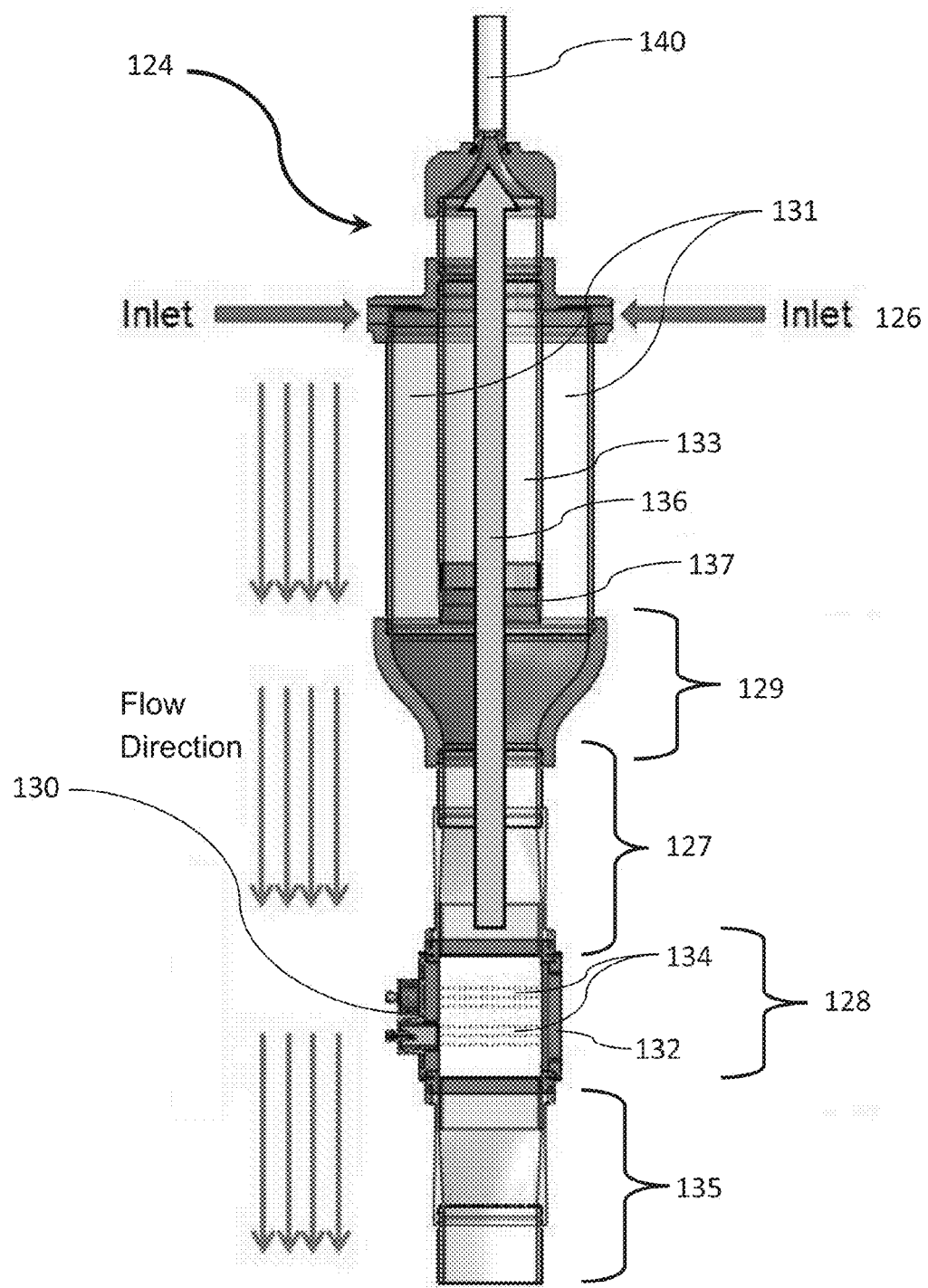
FIG. 4 is a cross-sectional view of an acoustophoretic separator in which the reflector of the present disclosure can be used.
Figure 5:
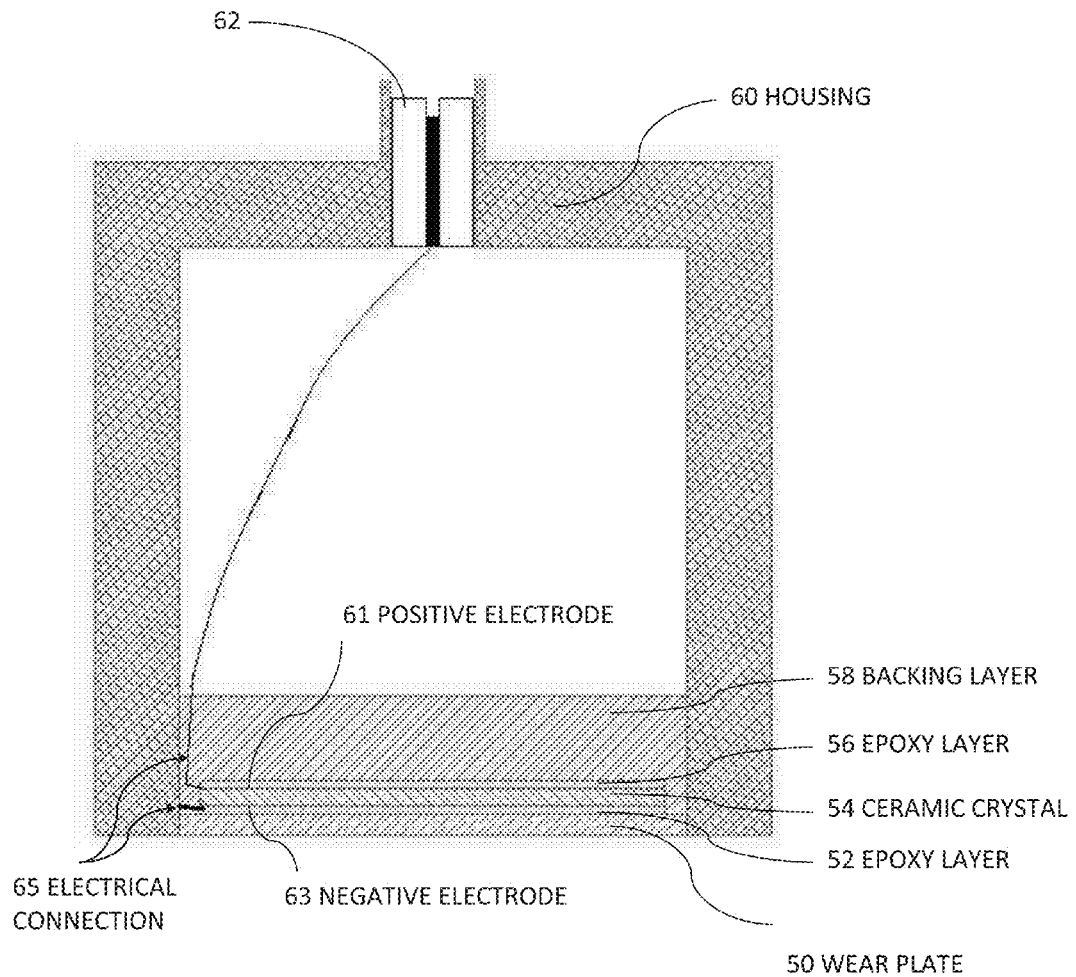
FIG. 5 is a cross-sectional diagram of a conventional ultrasonic transducer.

FIG. 4 is a cross-sectional view of an acoustophoretic separation apparatus in which the thin structure reflector of the present disclosure (e.g. a thin plastic film) can be used. This is a figure of a 4" by 2.5" flow cross sectional area intermediate scale apparatus 124 for separating a host fluid from a buoyant fluid or particulate. The acoustic path length is 4". The apparatus is shown here in an orientation where the flow direction is downwards, which is used for separating less-dense particles from the host fluid. However, the apparatus may be essentially turned upside down to allow separation of particles which are heavier than the host fluid. Instead of a buoyant force in an upward direction, the weight of the agglomerated particles due to gravity pulls them downward. It should be noted that this embodiment is depicted as having an orientation in which fluid flows vertically. However, it is also contemplated that fluid flow may be in a horizontal direction, or at an angle.

A particle-containing fluid enters the apparatus through inlets 126 into an annular plenum 131. The annular plenum has an annular inner diameter and an annular outer diameter. Two inlets are visible in this illustration, though it is contemplated that any number of inlets may be provided as desired. In particular embodiments, four inlets are used. The inlets are radially opposed and oriented.

A contoured nozzle wall 129 reduces the outer diameter of the flow path in a manner that generates higher velocities near the wall region and reduces turbulence, producing near plug flow as the fluid velocity profile develops, i.e. the fluid is accelerated downward in the direction of the centerline with little to no circumferential motion component and low flow turbulence. This generates a chamber flow profile that is optimum for acoustic separation and particle collection. The fluid passes through connecting duct 127 and into a flow/separation chamber 128. The contoured nozzle wall 129 also adds a radial motion component to the suspended particles, moving the particles closer to the centerline of the apparatus and generating more collisions with rising, buoyant agglomerated particles. This radial motion will allow for optimum scrubbing of the particles from the fluid in the connecting duct 127 prior to reaching the separation chamber. The contoured nozzle wall 129 directs the fluid in a manner that generates large scale vortices at the entrance of the collection duct 133 to also enhance particle collection. Generally, the flow area of the device 124 is designed to be continually decreasing from the annular plenum 131 to the separation chamber 128 to assure low turbulence and eddy formation for better particle separation, agglomeration, and collection. The nozzle wall has a wide end and a narrow end. The term scrubbing is used to describe the process of particle/droplet agglomeration, aggregation, clumping or coalescing, that occurs when a larger particle/droplet travels in a direction opposite to the fluid flow and collides with smaller particles, in effect scrubbing the smaller particles out of the suspension.

The flow/separation chamber 128 includes a transducer array 130 and reflector 132 on opposite sides of the chamber. The reflector can be the thin film-air interface described above in FIG. 1, with one side of the film exposed to the fluid within the flow chamber and the other side of the film exposed to the air outside of the flow chamber. In use, standing waves 134 are created between the transducer array 130 and thin film-air interface 132. These standing waves can be used to agglomerate particles, and this orientation is used to agglomerate particles that are buoyant (e.g. oil). Fluid, containing residual particles, then exits through flow outlet 135.

As the buoyant particles agglomerate, they eventually overcome the combined effect of the fluid flow drag forces and acoustic radiation force, and their buoyant force 136 is sufficient to cause the buoyant particles to rise upwards. In this regard, a collection duct 133 is surrounded by the annular plenum 131. The larger particles will pass through this duct and into a collection chamber 140. This collection chamber can also be part of an outlet duct. The collection duct and the flow outlet are on opposite ends of the apparatus.

It should be noted that the buoyant particles formed in the separation chamber 128 subsequently pass through the connecting duct 127 and the nozzle wall 129. This causes the incoming flow from the annular plenum to flow over the rising agglomerated particles due to the inward radial motion imparted by the nozzle wall. This allows the rising particles to also trap smaller particles in the incoming flow, increasing scrubbing effectiveness. The length of the connecting duct 127 and the contoured nozzle wall 129 thus increase scrubbing effectiveness. Especially high effectiveness is found for particles with a size of 0.1 microns to 20 microns, where efficiency is very low for conventional methods.

The design here provides an optimized velocity profile with low flow turbulence at the inlet to the flow chamber 128, a scrubbing length before the flow chamber to enhance particle agglomeration and/or coalescence before acoustic separation, and the use of the collection vortices to aid particle removal at the collection duct 133.

The transducer setup of the present disclosure creates a three dimensional pressure field which includes standing waves perpendicular to the fluid flow. The pressure gradients are large enough to generate acoustophoretic forces orthogonal to the standing wave direction (i.e., the acoustophoretic forces are parallel to the fluid flow direction) which are of the same order of magnitude as the acoustophoretic forces in the wave direction. This permits enhanced particle trapping, clumping and collection in the flow chamber and along well-defined trapping lines, as opposed to merely trapping particles in collection planes as in conventional devices. The particles have significant time to move to nodes or antinodes of the standing waves, generating regions where the particles can concentrate, agglomerate, and/or coalesce, and then gravity separate.

In some embodiments, the fluid flow has a Reynolds number of up to 1500, i.e. laminar flow is occurring. For practical application in industry, the Reynolds number is usually from 10 to 1500 for the flow through the system. The particle movement relative to the fluid motion generates a particle Reynolds number much less than 1.0 for that particle. The Reynolds number represents the ratio of inertial flow effects to viscous effects in a given flow field. For Reynolds numbers below 1.0, viscous forces are dominant in the flow field. This results in significant damping where shear forces are predominant throughout the flow. This flow where viscous forces are dominant is called Stokes flow. Wall contouring and streamlining have very little importance under such conditions. This is associated with the flow of very viscous fluids or the flow in very tiny passages, like MEMS devices.

The large annular plenum is followed by an inlet wall nozzle that accelerates and directs the fluid inward toward the centerline as shown in FIG. 4. The wall contour will have a large effect on the profile. The area convergence increases the flow average velocity, but it is the wall contour that determines the velocity profile. The nozzle wall contour will be a flow streamline, and is designed with a small radius of curvature in the separator.

It may be helpful now to describe the ultrasonic transducer(s) used in the acoustophoretic filtering device in more detail. FIG. 5 is a cross-sectional diagram of a conventional ultrasonic transducer. This transducer has a wear plate 50 at a bottom end, epoxy layer 52, ceramic crystal 54 (made of, e.g. PZT), an epoxy layer 56, and a backing layer 58. On either side of the ceramic crystal, there is an electrode: a positive electrode 61 and a negative electrode 63. The epoxy layer 56 attaches backing layer 58 to the crystal 54. The entire assembly is contained in a housing 60 which may be made out of, for example, aluminum. An electrical adapter 62 provides connection for wires to pass through the housing and connect to leads (not shown) which attach to the crystal 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

FIG. 6 is a cross-sectional view of an ultrasonic transducer 81 of the present disclosure. Transducer 81 is shaped as a disc or a plate, and has an aluminum housing 82. The piezoelectric crystal is a mass of perovskite ceramic crystals, each consisting of a small, tetravalent metal ion, usually titanium or zirconium, in a lattice of larger, divalent metal ions, usually lead or barium, and $O^{2-}$ ions. As an example, a PZT (lead zirconate titanate) crystal 86 defines the bottom end of the transducer, and is exposed from the exterior of the housing. The crystal is supported on its perimeter by a small elastic layer 98, e.g. silicone or similar material, located between the crystal and the housing. Put another way, no wear layer is present.

Screws 88 attach an aluminum top plate **82*a* of the housing to the body 82*b* of the housing via threads. The top plate includes a connector 84 for powering the transducer. The top surface of the PZT crystal 86 is connected to a positive electrode 90 and a negative electrode 92, which are separated by an insulating material 94. The electrodes can be made from any conductive material, such as silver or nickel. Electrical power is provided to the PZT crystal 86 through the electrodes on the crystal. Note that the crystal 86 has no backing layer or epoxy layer. Put another way, there is an air gap 87 in the transducer between aluminum top plate 82*a* and the crystal 86 (i.e. the air gap is completely empty). A minimal backing 58 and/or wear plate 50 may be provided in some embodiments, as seen in FIG. 7**.

The transducer design can affect performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the crystal to vibrate in one of its eigenmodes with a high Q-factor. The vibrating ceramic crystal disk or plate is directly exposed to the fluid flowing through the flow chamber.

Removing the backing (e.g. making the crystal air backed) also permits the ceramic crystal to vibrate at higher order modes of vibration with little damping (e.g. higher order modal displacement). In a transducer having a crystal with a backing, the crystal vibrates with a more uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines.

In some embodiments, the crystal may have a backing that minimally affects the Q-factor of the crystal. The backing may be made of a substantially acoustically transparent material such as balsa wood, foam, or cork which allows the crystal to vibrate in a higher order mode shape and maintains a high Q-factor while still providing some mechanical support for the crystal. The backing layer may be a solid, or may be a lattice having holes through the layer, such that the lattice follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. This may be desirable in, for example, biological applications such as separating blood. Such applications might use a wear layer such as chrome, electrolytic nickel, or electroless nickel or glassy carbon. Chemical vapor deposition could also be used to apply a layer of poly(p-xylylene) (e.g. Parylene) or other polymer. Organic and biocompatible coatings such as silicone or polyurethane are also usable as a wear surface.

In the present systems, the system is operated at a voltage such that the particles are trapped in the ultrasonic standing wave. The particles are collected in well-defined trapping lines, separated by half a wavelength. Within each nodal plane, the particles are trapped in the minima of the acoustic radiation potential. The axial component of the acoustic radiation force drives the particles, with a positive contrast factor, to the pressure nodal planes, whereas particles with a negative contrast factor are driven to the pressure anti-nodal planes. The radial or lateral component of the acoustic radiation force is the force that traps, clumps, and gravity separates the particles. In systems using typical transducers, the radial or lateral component of the acoustic radiation force is typically several orders of magnitude smaller than the axial component of the acoustic radiation force. On the contrary, the lateral force in separator 1 can be significant, on the same order of magnitude as the axial force component, and is sufficient to overcome the fluid drag force at linear velocities of up to 1 cm/s. As discussed above, the lateral force can be increased by driving the transducer in higher order mode shapes, as opposed to a form of vibration where the crystal effectively moves as a piston having a uniform displacement. The types of waves thus generated can be characterized as composite waves, with displacement profiles that are similar to leaky symmetric (also referred to as compressional or extensional) Lamb waves. The waves are leaky because they radiate into the water layer, which result in the generation of the acoustic standing waves in the water layer. Symmetric Lamb waves have displacement profiles that are symmetric with respect to the neutral axis of the piezoelectric element, which causes multiple standing waves to be generated in a 3-D space. These higher order modes of vibration can include modes (1,1), (1,2), (2,1), (2,2), (2, 3), or (m, n), where m and n are 1 or greater. The acoustic pressure is proportional to the driving voltage of the transducer. The electrical power is proportional to the square of the voltage.

In some embodiments, the pulsed voltage signal driving the transducer can have a sinusoidal, square, sawtooth, or triangle waveform; and have a frequency of 500 kHz to 10 MHz. The pulsed voltage signal can be driven with pulse width modulation, which produces any desired waveform. The pulsed voltage signal can also have amplitude or frequency modulation start/stop capability to eliminate streaming.

The size, shape, and thickness of the transducer determine the transducer displacement at different frequencies of excitation, which in turn affects separation efficiency. Typically, the transducer is operated at frequencies near the thickness resonance frequency (half wavelength). Gradients in transducer displacement typically result in more places for particles to be trapped. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

Figure 8:
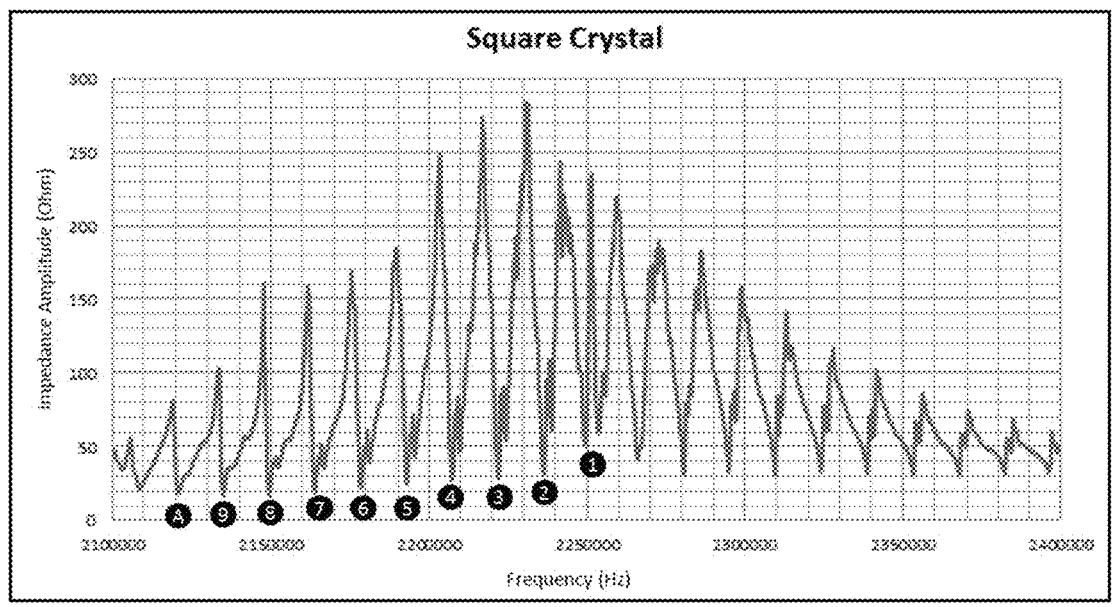
FIG. 8 is a graph of electrical impedance amplitude versus frequency for a square transducer driven at different frequencies.

To investigate the effect of the transducer displacement profile on acoustic trapping force and separation efficiencies, an experiment was repeated ten times using a 1"×1" square transducer, with all conditions identical except for the excitation frequency. Ten consecutive acoustic resonance frequencies, indicated by circled numbers 1-9 and letter A on FIG. 8, were used as excitation frequencies. The conditions were experiment duration of 30 min, a 1000 ppm oil concentration of approximately 5-micron SAE-30 oil droplets, a flow rate of 500 ml/min, and an applied power of 20 W. Oil droplets were used because oil is denser than water, and can be separated from water using acoustophoresis.

Figure 9:
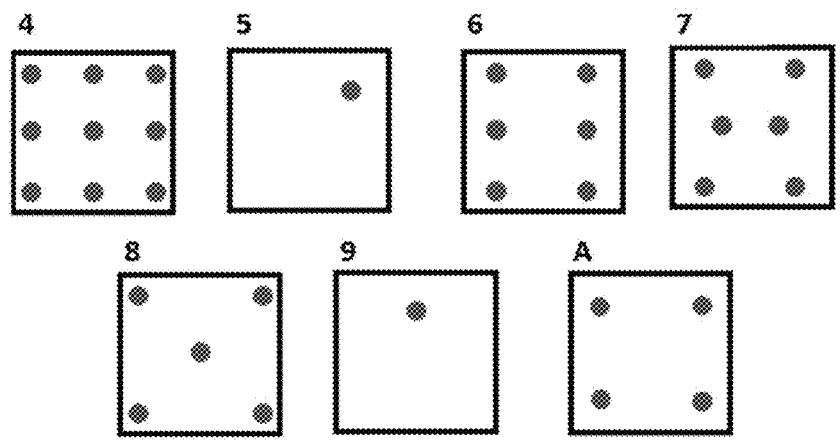
FIG. 9 illustrates the trapping line configurations for seven of the peak amplitudes of FIG. 8 from the direction orthogonal to fluid flow.

FIG. 9 shows the measured electrical impedance amplitude of the transducer as a function of frequency in the vicinity of the 2.2 MHz transducer resonance when operated in a water column containing oil droplets. The minima in the transducer electrical impedance correspond to acoustic resonances of the water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. As an example, at one frequency of excitation with a single line of trapped oil droplets, the displacement has a single maximum in the middle of the electrode and minima near the transducer edges. At another excitation frequency, the transducer profile has multiple maxima leading to multiple trapped lines of oil droplets. Higher order transducer displacement patterns result in higher trapping forces and multiple stable trapping lines for the captured oil droplets.

As the oil-water emulsion passed by the transducer, the trapping lines of oil droplets were observed and characterized. The characterization involved the observation and pattern of the number of trapping lines across the fluid channel, as shown in FIG. 9, for seven of the ten resonance frequencies identified in FIG. 8. Different displacement profiles of the transducer can produce different (more) trapping lines in the standing waves, with more gradients in displacement profile generally creating higher trapping forces and more trapping lines.

The transducer(s) is/are used to create a pressure field that generates forces of the same order of magnitude both orthogonal to the standing wave direction and in the standing wave direction. When the forces are roughly the same order of magnitude, particles of size 0.1 microns to 300 microns will be moved more effectively towards regions of agglomeration ("trapping lines"). Because of the equally large gradients in the orthogonal acoustophoretic force component, there are "hot spots" or particle collection regions that are not located in the regular locations in the standing wave direction between the transducer 130 and the reflector 132. Hot spots are located at the minima of acoustic radiation potential. Such hot spots represent particle collection locations.

Figure 10:
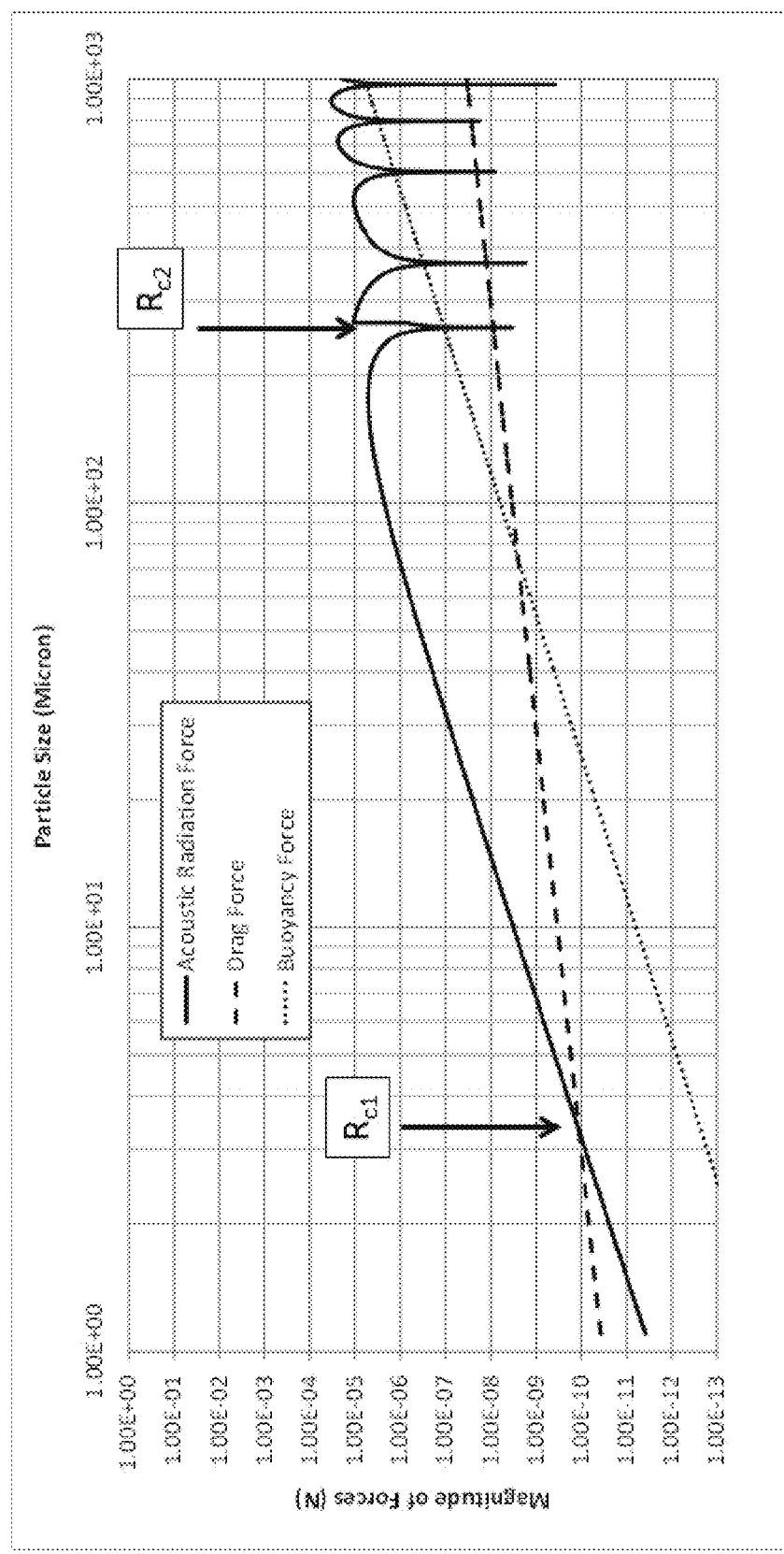
FIG. 10 is a graph showing the relationship of the acoustic radiation force, buoyancy force, and Stokes' drag force to particle size. The horizontal axis is in microns ($\mu$m) and the vertical axis is in Newtons (N).

FIG. 10 is a log-log graph (logarithmic y-axis, logarithmic x-axis) that shows the scaling of the acoustic radiation force, fluid drag force, and buoyancy force with particle radius. Calculations are done for a typical SAE-30 oil droplet used in experiments. The buoyancy force is a particle volume dependent force, and is therefore negligible for particle sizes on the order of micron, but grows, and becomes significant for particle sizes on the order of hundreds of microns. The fluid drag force scales linearly with fluid velocity, and therefore typically exceeds the buoyancy force for micron sized particles, but is negligible for larger sized particles on the order of hundreds of microns. The acoustic radiation force scaling acts differently. When the particle size is small, the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when a suspension is flowing through the system with primarily small micron sized particles, it is necessary for the acoustic radiation force to balance the combined effect of fluid drag force and buoyancy force for a particle to be trapped in the standing wave. In FIG. 10 this happens for a particle size of about 3.5 micron, labeled as $R_{c1}$. The graph then indicates that all larger particles will be trapped as well. Therefore, when small particles are trapped in the standing wave, particles coalescence/clumping/aggregation/agglomeration takes place, resulting in continuous growth of effective particle size. As the particle size grows, the acoustic radiation force reflects off the particle, such that large particles will cause the acoustic radiation force to decrease. Particle size growth continues until the buoyancy/gravity force becomes dominant, which is indicated by a second critical particle size, $R_{c2}$, at which size the particles will rise or sink, depending on their relative density with respect to the host fluid. Thus, FIG. 10 explains how small particles can be trapped continuously in a standing wave, grow into larger particles or clumps, and then eventually will rise or settle out because of increased buoyancy/gravity force.

In biological applications, it is contemplated that all of the parts of the system (e.g. the reaction vessel, tubing leading to and from the bioreactor, the temperature-regulating jacket, etc.) can be separated from each other and be disposable. The frequency of the transducers may also be varied to obtain optimal effectiveness for a given power.

The following examples are provided to illustrate the apparatuses, components, and methods of the present disclosure. The examples are merely illustrative and are not intended to limit the disclosure to the materials, conditions, or process parameters set forth therein.

EXAMPLES

Example 1

A polyolefin heat shrink film having a thickness of 0.60 mills (15.24 microns) was used as the acoustically transparent film to form a fluid-air interface, and was sandwiched in place using an empty transducer housing. This thickness is ⅕₀ of a wavelength when the transducer is operated at a frequency of 2.2 MHz. FIG. 3A is a picture of the test device.

FIG. 3B is a picture of the plastic film-air interface reflector during operation. The operation of a 5×5 trapping line mode can be seen through the plastic film, which is also optically transparent. The white trapping lines are visible through the plastic film. The overall efficiency of the apparatus dropped only 3% compared to using a steel reflector, which was within the range of measurement error.

Example 2

Acoustically transparent thin films 170 were attached to the face of the piezoelectric crystal (dimensions 1 inch by 1 inch) 172 of the ultrasonic transducer. Two different plastic thin films were used, one about 60 microns thick and one about 350 microns thick. A thin layer of ultrasonic transmission gel 174 was used to ensure there were no air pockets between the thin film and the crystal face. FIG. 11 is a picture of the square transducer and a diagram of the resulting structure.

Three types of reflectors were tested: a steel reflector, a thin plastic film reflector about 60 microns thick (R-ATF), and a thin plastic film reflector about 350 microns thick (R-TBC). Three different types of piezoelectric crystals were used: a crystal with the plastic thin film cover about 60 microns thick (C-ATF); a crystal with the plastic thin film cover about 350 microns thick (C-TBC); and an uncoated gamma sterilized crystal (UC).

These crystal/reflector combinations were tested to determine the effect on separation of a 3% yeast feed having 200 million cells/mL and starting turbidity as indicated. The feed flow rate was 30 ml/min, the concentrate output was 5 mL/min, and the permeate output was 25/mL/min. The power to the crystals was 7-11 watts, unless otherwise noted, and the frequency was 2.2455 MHz. The 350-micron-thick film was about one-half the thickness of the wavelength at this frequency.

After 30 minutes, the concentrate, permeate, and retentate were measured. The concentrate was the portion exiting the device that contained the concentrated yeast, along with some fluid. The permeate was the filtered portion exiting the device, which was mostly liquid with a much lower concentration of yeast. The retentate was the remaining substance left in the device after operation.

The results are provided in the following Table 1.

TABLE 1

| Reflector | Crystal | Starting Turbidity (NTU) | Turbidity Reduction (%) | Permeate Turbidity (NTU) | Concentrate Turbidity (NTU) | Retentate Turbidity (NTU) |
| --- | --- | --- | --- | --- | --- | --- |
| Steel | UC | 5400 | 97 | 164 | 24000 | 7760 |
| R-ATF | UC (8 watts) | 5690 | 95 | 309 | 23440 | 8210 |
| R-ATF | UC (11 watts) | 5520 | 91 | 308 | 22480 | 9530 |
| Steel | C-ATF | 5130 | 98 | 134 | 24520 | 6600 |
| Steel | C-TBC | 5420 | 91 | 450 | 28160 | 8070 |
| R-TBC | UC | 5730 | 91 | 432 | 29480 | 8190 |
| R-TBC | C-TBC (10-11 watts) | 5840 | 88 | 660 | 24120 | 7500 |
| R-TBC | C-TBC (19-20 watts) | 5690 | 93 | 379 | 31080 | 8700 |

As seen here, the turbidity was heavily reduced in the permeate and heavily increased in the concentrate, indicating the efficiency of the system.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An apparatus, comprising:
a flow chamber having at least one inlet and at least one outlet;
at least one ultrasonic transducer located on a wall of the flow chamber, the transducer including a piezoelectric material driven by a voltage signal to create a multi-dimensional acoustic standing wave in the flow chamber; and
a thin structure located on a wall opposite the at least one ultrasonic transducer, the thin structure providing a pressure release boundary that acts as a reflector.

2. The apparatus of claim 1, wherein the thin structure is a plastic film.

3. The apparatus of claim 2, wherein the plastic film is made of a material selected from the group consisting of olefins, polyurethanes, polyureas, polyesters, polystyrenes, polyamides, cellulosics, ionomers, polyvinyl chloride, polyvinyl butyral, polyvinylidene fluoride, polyvinylidene chloride, ethylene vinyl acetate, ethylene tetrafluoroethylene, polytetrafluoroethylene, and combinations thereof.

4. The apparatus of claim 1, wherein the thin structure is transparent.

5. The apparatus of claim 1, wherein the thin structure is substantially flat.

6. The apparatus of claim 1, wherein the thin structure has a thickness that is ½ or less of the wavelength emitted by the at least one ultrasonic transducer.

7. The apparatus of claim 1, wherein the transducer includes a housing containing the piezoelectric material.

8. The apparatus of claim 7, wherein the piezoelectric material does not have a backing layer.

9. The apparatus of claim 7, wherein the piezoelectric material is backed by a substantially acoustically transparent material.

10. The apparatus of claim 9, wherein the substantially acoustically transparent material is balsa wood, cork, or a foam.

11. The apparatus of claim 9, wherein the substantially acoustically transparent material has a thickness of up to one inch.

12. The apparatus of claim 9, wherein the substantially acoustically transparent material is in the form of a lattice.

13. The apparatus of claim 7, wherein the ultrasonic transducer has a face that contacts fluid within the flow chamber, the face being coated with a wear layer comprising chrome, electrolytic nickel, electroless nickel, p-xylylene, glassy carbon, or urethane.

14. The apparatus of claim 1, wherein the piezoelectric material is a ceramic crystal.

15. The apparatus of claim 1, further comprising:
an apparatus inlet that leads to an annular plenum;
a contoured nozzle wall downstream of the apparatus inlet;
a collection duct surrounded by the annular plenum; and
a connecting duct joining the contoured nozzle wall to the flow chamber inlet.

16. The apparatus of claim 1, comprising a plurality of transducers that span the width of the flow chamber.

17. A method of separating a second fluid or a particulate from a host fluid, comprising:
flowing a mixture of the host fluid and the second fluid or particulate through an apparatus, the apparatus comprising:
a flow chamber having at least one inlet and at least one outlet;
an ultrasonic transducer located on a wall of the flow chamber, the transducer including a piezoelectric material driven by a voltage signal to create a multi-dimensional acoustic standing wave in the flow chamber; and
a thin structure located on a wall opposite the at least one ultrasonic transducer, the thin structure providing a pressure release boundary that acts as a reflector; and
capturing smaller particles of the second fluid or particulate in the multi-dimensional acoustic standing wave to clump, aggregate, and coalesce and continuously gravity separate the second fluid or particulate from the host fluid.

18. The method of claim 17, wherein the particulate is Chinese hamster ovary (CHO) cells, NS0 hybridoma cells, baby hamster kidney (BHK) cells, insect cells, or human cells.

19. The method of claim 17, wherein the host fluid is continuously flowed through the flow chamber.

20. The method of claim 17, wherein the multi-dimensional acoustic standing wave has an axial force and a lateral force, the lateral force being at least the same order of magnitude as the axial force.

21. An apparatus, comprising:
- a flow chamber having at least one inlet and at least one outlet;
- at least one ultrasonic transducer located on a wall of the flow chamber, the transducer including a piezoelectric material driven by a voltage signal to create a multi-dimensional acoustic standing wave in the flow chamber; and
- a thin structure located on a wall opposite the at least one ultrasonic transducer, the thin structure providing a pressure release boundary that acts as a reflector, wherein the apparatus has an acoustic reflection coefficient from −0.1 to −1.0.

* * * * *